United States Patent [19]
McCarty et al.

[11] Patent Number: 5,914,326
[45] Date of Patent: Jun. 22, 1999

[54] METHOD FOR PROMOTING WEIGHT AND FAT LOSS

[75] Inventors: Mark F. McCarty, San Diego; John Gustin, Carlsbad, both of Calif.

[73] Assignee: AMBI Inc., Purchase, N.Y.

[21] Appl. No.: 08/908,820

[22] Filed: Aug. 8, 1997

[51] Int. Cl.$^6$ .................................................. A61K 3/555
[52] U.S. Cl. ........................ 514/188; 514/505; 424/655
[58] Field of Search .......................... 424/655; 514/556, 514/506, 547, 557, 392, 387, 188, 505

[56] References Cited

U.S. PATENT DOCUMENTS

| | | | |
|---|---|---|---|
| 4,548,937 | 10/1985 | Stanko ..................................... | 514/251 |
| 5,087,623 | 2/1992 | Boynton et al. ......................... | 514/188 |

FOREIGN PATENT DOCUMENTS 0 787 489 A2  8/1997  European Pat. Off. .

OTHER PUBLICATIONS

Argaud, et al., Metformin decreases gluconeogenesis by enhancing the pyruvate kinase flux in isolated . . . , Eur. J. Biochem. 213:1341–1348 (1993).
Berry, et al., The Calorigenic Nature of Hepatic Ketogenesis: An Explanation for the Stimulation . . . , Eur. J. Biochem. 131:205–214 (1983).
Clarke, et al., Comparison of metformin and chlorpropamide in non–obese, maturity–onset diabetics . . . , British Med. Jour. 2:1576–1578 (1977).
Conway, et al., A new approach for the estimation of body composition: infrared interactance, The Am. J. of Clin. Nutr. 40:1123–1130 (1984).
Cortez, et al., Effects of pyruvate and dihydroxyacetone consumption on the growth and metabolic . . . , The Am. J. of Clin. Nutr. 53:847–853 (1991).
Elia, et al., Evaluation of near infra–red interactance as a method for predicting body composition, Eur. J. of Clin. Nutr. 44:113–121 (1990).
Kaats, et al., Effects of Chromium Picolinate Supplementation on Body Composition: a Randomized, . . . , Curr. Thera. Res. 57(10):747–756 (1996).
Lee, et al., Metformin Decreases Food Consumption in Obese Non–Insulin–Dependent (NIDDM) Diabetics, Diabetes 4(Suppl.2) 170A.
Mabrouk, et al., Acute Hormonal Control of Acetyl–CoA Carboxylase, J. Biol. Chem. 265(11):6330–6338 (1990).
McCarty, M.F., Promotion of Hepatic Lipid Oxidation and Gluconeogenesis as a Strategy for Appetite Control, Medical Hypotheses 42:215–225 (1994).
McCarty, MF., Inhibition of Citrate Lyase May Aid Aerobic Endurance, Medical Hypotheses 45:247–254 (1995).
McGarry, et al., Role of carnitine in hepatic ketogenesis, Proc. Nat. Acad. Sci. USA 72(11):4385–4388 (1975).
McGarry, et al., Regulation of Hepatic Fatty Acid Oxidation and Ketone Body Production, Ann. Rev. Biochem. 49:395–420 (1980).
Pegorier, et al., Induction of ketogenesis and fatty acid oxidation by glucagon and cyclic AMP in cultured . . . , Biochem. J. 264:93–100 (1989).
Stanko, et al., Inhibition of Lipid Accumulation and Enhancement of Energy Expenditure by the Addition . . . , Metabolism, 35(2):182–186 (1986).
Stanko, et al., Reduction of Carcass Fat in Swine with Dietary Addition of Dihydroxyacetone and Pyruvate, J. Anim. Sci 67:1272–1278 (1989).
Stanko, et al., Body composition, energy utilization, and nitrogen metabolism with a severely . . . , Am. J. Clin. Nutr. 55:771–776 (1992).
Stanko, et al., Body composition, energy utilization, and nitrogen metabolism with a 4.25–MJ/d . . . , Am. J. Clin. Nutr. 56:630–635 (1992).
Stanko, et al., Pyruvate supplementation of a low–cholesterol, low–fat diet: effects on plasma lipid . . . , Am. J. Clin. Nutr. 59:423–427 (1994).
Stanko, et al., Inhibition of regain in body weight and fat with addition of 3–carbon compounds to the diet . . . , Inter. J. Obesity 20:925–930 (1996).
Stumvoll, et al., Metabolica Effects of Metformin in Non–Insulin–Dependent Diabetes Mellitus, N. Engl. J. Med. 333(9):550–554 (1995).

*Primary Examiner*—Frederick Krass
*Attorney, Agent, or Firm*—Knobbe, Martens, Olson & Bear, LLP

[57] ABSTRACT

A method for promoting weight and fat loss comprising administering to an individual in need thereof hydroxycitrate, carnitine and an agent which promotes the rapid intramitochondrial generation of oxaloacetate or induces endogenous production of pyruvate. This method also promotes an increase in lean body mass.

16 Claims, No Drawings

METHOD FOR PROMOTING WEIGHT AND FAT LOSS

FIELD OF THE INVENTION

The present invention relates to a method for promoting fat loss. More particularly, the invention relates to coadministration of hydroxycitrate, carnitine and a compound which increases mitochondrial synthesis of oxaloacetate.

BACKGROUND OF THE INVENTION

The combination of hydroxycitrate (HCA) and carnitine has been recommended as a diet aid based on its presumed ability to promote the transport of free fatty acids (FFAs) into hepatic mitochondria, a major site of fatty acid oxidation (McCarty, M., *Med. Hypoth.* 42:215–225, 1994; McCarty, M., *Med. Hypoth.* 45:247–254, 1995). This transport step is believed to be rate-limiting for hepatic ketogenesis (McGarry et al., *Proc. Natl. Acad. Sci. U.S.A.* 72:4385–4388, 1975; McGarry et al., *Annu. Rev. Biochem.* 49:395–420, 1980).

More specifically, the conversion of cytoplasmic fatty acyl coA to fatty acyl carnitine via the enzyme carnitine palmitoyl transferase I (CPT) is pace-setting for fatty acid transport into mitochondria and thus for ketogenesis in which fatty acids are oxidized (McGarry et al., supra.). HCA, the main acid found in fruits of the genus Garcinia, disinhibits CPT by suppressing synthesis of malonyl coA, a key allosteric inhibitor of this enzyme. Carnitine is the essential cofactor for CPT activity, and ordinary non-fasting hepatocyte levels of this enzyme appear to be subsaturating, such that provision of extra carnitine accelerates hepatic ketogenesis when CPT is activated.

Although the process of ketogenesis reduces both nicotinamide adenine dinucleotide (NAD+) and flavin adenine dinucleotide (FAD), ketogenesis can proceed at a high rate even when hepatocyte metabolism is generating ADP at a low rate. Berry et al. (*Eur. J. Biochem.*, 131:205–214, 1983) suggest that during ketogenesis, high energy electrons enter the respiratory chain at a greater rate than hepatocytes can generate ADP, resulting in an electron glut and an increased electrochemical proton gradient. Under these circumstances, electrons entering the chain at the level of coenzyme Q (CoQ) (via the FAD-dependent acyl coA dehydrogenase reaction) can be "pushed" up the respiratory chain to AND dehydrogenase which transfers them to NAD+. These electrons can then be transported to the cytosol via the malate/aspartate shuttle and, after reducing NAD+ or NAD(P) in the cytosol, can then re-enter the mitochondrial respiratory chain at the CoQ level via the glycerol-3-phosphate shuttle. The "reverse electron transport" step in this cycle is driven by the electrochemical proton gradient of the mitochondrial inner membrane—which diminishes as a result—or, alternatively, by the conversion of ATP to ADP via the mitochondrial ATP synthase. After two "turns" of this cycle, the electrochemical proton gradient will be sufficiently diminished to enable the electrons to pass down the respiratory chain from CoQ to oxygen, without any coupling to ATP synthesis. Alternatively, the two ADP generated by two turns of the cycle will enable the coupled transport of these electrons from CoQ to oxygen. This mechanism would effectively "uncouple" the transfer of electrons from $FADH_2$ to oxygen during ketogenesis, thus resulting in continuous fatty acid oxidation and consequent fat loss.

Pyruvate has also been shown to exert a fat loss-promoting effect (Stanko et al., *Metabolism* 35:182–186, 1986; Stanko et al., *J. Animal Sci.* 67:1272–1278, 1989; Cortez et al., *Am. J. Clin. Nutr.* 53:847–853, 1991; Stanko et al., *Am. J. Clin. Nutr.* 55:771–776, 1992; Stanko et al., *Am. J. Clin. Nutr.* 56:630–635, 1992; Stanko et al., *Int. J. Obesity* 20:925–930, 1996).

There is a constant need for methods of promoting weight and fat loss. The present invention provides such a method.

SUMMARY OF THE INVENTION

One embodiment of the present invention is a method of promoting weight and fat loss in an individual in need thereof, comprising coadministering to the individual daily effective weight and fat loss-promoting amounts of hydroxycitrate, carnitine and an agent which promotes the rapid intramitochondrial generation of oxaloacetate or induces endogenous production of pyruvate. Preferably, the effective amount of hydroxycitrate is between about 1 and 10 grams. More preferably, the effective amount of hydroxycitrate is between about 1 and 5 grams. Preferably, the effective amount of carnitine is between about 100 and 1,000 milligrams. More preferably, effective amount of carnitine is between about 100 and 500 mg. Advantageously, the effective amount of the agent, with the exception of biotin, is between about 1 and 100 grams. More advantageously, the effective amount of the agent, with the exception of biotin, is between about 1 and 25 grams. In one aspect of this preferred embodiment, the agent which promotes rapid intramitochondrial generation of oxaloacetate is pyruvate, lactic acid, aspartic acid, serine or glycine. Preferably, the agent which promotes endogenous production of pyruvate is metformin or biotin. Preferably, the amount of biotin is between about 5 mg and 50 mg. Advantageously, the amount of metformin is between about 1 mg and 3 mg. The method may further comprise administering an effective daily weight and fat loss promoting amount of chromium as chromic tripicolinate. Preferably, the effective amount is about 400–1,000 micrograms. More preferably, the effective amount is about 600 micrograms.

The present invention also provides a pharmaceutical composition comprising hydroxycitrate, carnitine and an agent which promotes the rapid intramitochondrial generation of oxaloacetate or induces endogenous production of pyruvate, wherein the ratio of hydroxycitrate to carnitine to agent is between about 2:1:2 and 10:1:100 (w/w). Preferably, the agent which promotes rapid intramitochondrial generation of oxaloacetate is pyruvate, lactic acid, aspartic acid, serine or glycine. Advantageously, the agent which promotes endogenous production of pyruvate is metformin or biotin.

DETAILED DESCRIPTION OF THE PREFERRED EMBODIMENTS

The present invention includes the observation that joint administration of pyruvate, HCA and carnitine to obese subjects promoted a remarkable rate of body fat loss and thermogenesis, strongly suggestive of uncoupled fatty acid oxidation. The observed effect was synergistic. Without wishing to be bound by any particular theory, it is believed that pyruvate enhances the efficiency of the shuttle mechanisms required for reverse electron transport by serving as a biosynthetic precursor for key substrates of these shuttles, namely oxaloacetate and dihydroxyacetone phosphate. When concurrent administration of HCA/carnitine disinhibits hepatic ketogenesis, flooding hepatic mitochondria with reducing equivalents and initiating reverse electron transport, the pyruvate-mediated activation of shuttle mechanisms may substantially amplify the rate of reverse electron transport such that not only ketogenesis, but also Krebs cycle activity is at least partially uncoupled, enabling the complete oxidation of FFAs to $CO_2$ with little net production of ATP and a substantial release of heat.

The efficient conversion of pyruvate to mitochondrial oxaloacetate may be crucial to pyruvate's ability to synergize with HCA/carnitine. The rapid production of acetyl coA during ketogenesis can be expected to strongly activate pyruvate carboxylase, whereas pyruvate dehydrogenase will be inhibited. Moreover, the generation of ketone bodies from excess acetyl coA promotes pyruvate transport into mitochondria. Thus, pyruvate administered during ketogenesis should be rapidly converted to oxaloacetate, much of which is reduced to malate which readily exits mitochondria. Thus, pyruvate can catalyze the transfer of high energy electrons from mitochondria to the cytosol.

It is also contemplated that any agent capable of promoting the rapid intramitochondrial generation of oxaloacetate will also synergize with HCA/carnitine in promoting fat loss. Oxaloacetate itself will not be effective because it cannot directly enter mitochondria. Such agents include aspartic acid, lactic acid, serine and glycine. Aspartate is avidly transported into mitochondria and deaminated to yield oxaloacetate as a key portion of the malate-aspartate shuttle. Lactic acid is readily converted to pyruvate; however, the oxidation of lactate to pyruvate is expected to increase cytoplasmic redox potential which could slow the rate of electron transport from mitochondria to the cytoplasm. The amino acids serine and glycine also serve as pyruvate precursors and do not mediate such reductions when converted to pyruvate.

The use of agents which enhance the endogenous generation of pyruvate, in conjunction with HCA/carnitine, is also within the scope of the invention. One such agent is the drug metformin which enhances endogenous generation of pyruvate by activating pyruvate kinase (Argaud et al., *Eur. J. Biochem.* 213:1341–1348, 1993). The ability of metformin itself to promote weight loss and decreased appetite in diabetics has been described (Clarke et al., *Brit. Med. J.* 2:1567–1578, 1977; Stumvoll et al., *New Engl. J. Med.* 333:550–554, 1995; Lee et al., *Diabetes* 45(Suppl. 2):170A, 1996).

An alternative or adjunctive approach to activating pyruvate kinase is administration of high doses of biotin. The recommended safe daily intake of biotin is 100–300 μg per day, however no toxic effects were observed in clinical studies when up to 200 mg was administered. Biotin was observed to lessen weight gain in a congenitally obese strain of rat despite slightly increasing food intake (Zhang et al., *J. Nutr. Sci. Vitaminol.* 42:517–526, 1996). A dose of 3 mg three times per day has been shown to aid glycemic control in human diabetics (Maebashi et al., *J. Clin. Biochem. Nutr.*, 14:211–218, 1993).

HCA, carnitine and pyruvate are commercially available from health food stores and/or chemical supply companies. In order to promote fat loss, it is anticipated that the dosage range of pyruvate orally administered to an individual will be between about 1 and 100 g/day. In a preferred embodiment, this amount is between about 1 and 25 g/day. It is also contemplated that daily dosages of the agents discussed above which are converted to intramitochondrial oxaloacetate or which promote formation of endogenous pyruvate are within these ranges with the exception of biotin and metformin which are adminstered in daily dosages of between about 5–50 mg and 1–3 g, respectively. With regard to the HCA component of the combination therapy, the preferred daily dosage is between about 1 g and 10 g. More preferably, the daily dosage is between about 1 g and 5 g. The carnitine component is preferably administered at a daily dosage range of between about 100 and 1,000 mg, more preferably between about 100 mg and 500 mg.

Optionally, chromium tripicolinate may be administered along with the pyruvate, HCA and carnitine. This compound is available from drug stores and health food stores. In a controlled study evaluating the impact of this nutrient on body composition in overweight subjects (400–800 μg chromium daily), a significant incremental fat loss (relative to placebo) averaging 0.4 kg (0.9 lb) per month was observed (Kaats et al., *Curr. Ther. Res.* 57:747–756, 1996). In a preferred embodiment, the amount of chromium administered daily as chromic tripicolinate is between about 400 and 1,000 μg. In a more preferred embodiment, the daily amount of chromium administered as chromic tripicolinate is about 600 μg.

For oral administration, the components may be provided as a tablet, aqueous or oil suspension, dispersible powder or granule, emulsion, hard or soft capsule, syrup or elixir. Compositions intended for oral use may be prepared according to any method known in the art for the manufacture of pharmaceutically acceptable compositions. Pharmaceutically acceptable means that the agent should be acceptable in the sense of being compatible with the other ingredients of the formulation (as well as non-injurious to the patient). Such compositions may contain one or more of the following agents: sweeteners, flavoring agents, coloring agents and preservatives. The sweetening and flavoring agents will increase the palatability of the preparation. Tablets containing chromic tripicolinate in admixture with non-toxic pharmaceutically acceptable excipients suitable for tablet manufacture are acceptable. Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the components in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose. Such formulations may also contain a demulcent, a preservative, a flavoring or a coloring agent.

In the clinical study described in Example 1 below, patients were advised to perform fasting aerobic exercise and to eat substantial amounts of protein. Each of these measures is expected to increase glucagon activity. Glucagon promotes intramitochondrial fatty acid transport and ketogenesis, both by decreasing the synthesis of malonyl-coA and by decreasing the potency of malonyl-coA as an allosteric inhibitor of CPT (Mabrook et al., *J. Biol. Chem.* 265:6330–6338, 1996; Pegorier et al., *Biochem J.,* 264:93–100, 1989). Thus, measures which enhance glucagon activity have been recommended as adjuvants to HCA/carnitine administration (McCarty, *Med. Hypoth.* 45:247–254, 1995).

A clinical trial in which HCA, carnitine, pyruvate and chromium picolinate was administered to overweight volunteers, is described in the following example.

EXAMPLE 1

Clinical trial

A short pilot study was conducted to test the impact of a supplement regimen, in conjunction with dietary and exercise advice, on weight loss and physique modification in overweight volunteers. The daily regimen provided the following, to be consumed in three equal doses: calcium pyruvate, 12 g; HCA, 1.5 g; L-carnitine, 250 mg; chromium (as chromic tripicolinate), 600 μg. The supplements were to be consumed in the morning (prior to exercise or eating), with lunch and at bedtime. Participants were asked to walk at least 20 minutes each morning, on an empty stomach and at a brisk pace at which they could converse normally. Dietary advice consisted of recommendations to eat a high-protein, low-fat diet (30% and 10% of calories, respectively) in an amount that provided 0.75–1 g protein per pound of lean mass daily (or 100 g daily for women with lean mass under 100 pounds). These recommendations corresponded to total daily caloric intakes of 1,300–3,100 kcal daily, dependent on body size; the average recommended intake was about 2,000 kcal daily which was to be consumed in numerous small meals daily, and no calories were to be ingested in the three hours prior to bedtime.

Body composition was evaluated at baseline and at weekly intervals thereafter using Futrex 5000™, an infrared technique for quantifying the depth of underlying subcutaneous fat (Conway et al., *Am. J. Clin. Nutr.* 40:1123–1130, 1984; Elia et al., *Eur. J. Clin. Nutr.* 44:113–121, 1990). All measurements were made at a point a standardized distance up the upper arm between the heads of the biceps. On each occasion, except the last, measurements were taken in triplicate and averaged. Heights and weights were also determined, thus enabling calculation of body mass index (BMI), a standard measure of obesity which is defined as the weight divided by the square of the height.

A total of 23 volunteers, the majority Samoan-American, appeared for enrollment and admitted in three groups on dates A, B and C; final evaluation was on date D. The time periods between dates A-D, B-D and C-D were 28 days, 24 days and 21 days, respectively. Three subjects did not return after baseline evaluation, and one subject did not return for final evaluation. Two subjects refused to be weighed at baseline (insisting on "reporting" their own weights) and therefore could not be properly assessed. One subject developed a rash after three days, and pyruvate administration was discontinued. Thus, 16 of the participants were able to be evaluated. The initial body weights of the subjects ranged from 69 kg to 231 kg, with a mean weight of 117 kg. Percentage body fat ranged from 26% to 54%, with a mean value of 41%. The average BMI was 39.3 (range 26.2–63.7).

Most subjects tolerated the regimen quite well. As noted, one subject developed a rash and was discontinued in the study. The largest enrolled subject (initial weight 231 kg), who also lost the most weight and fat, had a prior history of gout, and experienced an attack of gout during the final week which prevented him from walking. One subject noted borborygmus (intestinal rumbling) and gas.

Most subjects reported feeling warm during the study, in the first week, three subjects reported sweating and/or subjective feelings of heat (including a woman who at baseline had complained that she was always cold). Since this was thought to be a possible sign of increased thermogenesis, the other subjects were queried as to whether they were experiencing sensations of warmth, and the subjects were virtually unanimous in affirming this. On subject (again, the largest one) noted profuse sweating and indicated that he needed to turn a fan on himself at bedtime in order to sleep. The other virtually unanimous subjective response was of considerably increased physical energy.

Self-reported compliance with the dietary and exercise recommendations was excellent in many subjects, but others confessed to occasional junk food binges, a failure to achieve the suggested intake of protein or sporadic adherence to morning walking exercise. Self-reported compliance with the supplement regimen in general was quite good, although a few subjects noted that they had missed several doses. Participants were free living and, with the exception of a whey supplement provided to several subjects, their food was self-chosen. Exercise was not monitored. Thus, the conditions of the study were closer to "real world" application than is the case in most carefully supervised clinical studies. Furthermore, no subjects were excluded from the final analysis owing to sporadic (or, in a few instances, non-existent) compliance with dietary, exercise or supplementation recommendations.

Since subjects were enrolled for varying period of time (3–4 weeks), results are reported as average weight loss and average fat loss per week. In the entire group of 16 subjects, average weekly weight loss was 1.5 kg (3.3 lb) and average weekly fat loss was 2.3 kg (5.1 lb). This implies a weekly gain of lean mass averaging 0.8 kg. The largest subject achieved, within 24 days, a weight loss of 11.8 kg (26 lb) and, remarkably, a fat loss of 22.7 kg (50 lb). If this subject is excluded from the analysis as atypical, the average weekly weight and fat losses in the remaining 15 subjects were 1.4 kg (3.1 lb) and 2.0 kg (4.4 lb), respectively.

Since grossly obese subjects have often been noted to lose significant weight initially when their diet is regulated (preventing binges on favorite foods), a separate analysis was made of the five subjects with an initial weight under 200 pounds (91 kg). In these subjects, average weekly weight loss and fat loss averaged 1.3 kg (2.9 lb) and 1.8 kg (4 lb), respectively which was not greatly different from the group as a whole. The subject with the lowest body weight, as well as the subject with the lowest initial percentage body fat, achieved weekly rates of fat loss of 2.0 and 2.7 kg (4.4 and 6 lb), respectively. Thus, the benefit does not appear to be contingent on severe obesity. The poorest response was noted in a 74 kg woman who lost 3.2 kg ((7 lb) and 4.5 kg (9.9 lb) of fat over four weeks. During the final week, she had been completely noncompliant with the diet and exercise recommendations.

These results demonstrate a marked synergism between pyruvate and HCA/carnitine. When used in conjunction with low-calorie diets or an overfeeding regimen, pyruvate (at 15–30 g daily) diminished body fat by about 1 kg over 21 days relative to placebo (Stanko et al., *Am. J. Clin. Nutr.* 55:771–776, 1992; Stanko et al., *Am. J. Clin. Nutr.* 56:630–635, 1992; Stanko et al., *Int. J. Obesity* 20:925–930, 1996). In the context of a low-fat weight-maintaining regimen in hyperlipidemic subjects, about half of whom were obese, the incremental fat loss associated with pyruvate (22–44 g daily) was 0.4 kg over six weeks (Stanko et al., *Am. J. Clin. Nutr.* 59:423–427, 1994). In a double-blind study in which overweight volunteers received HCA/carnitine/chromium picolinate while asked to avoid fatty foods, eat more fiber, and get more physical activity, the additional fat loss attributable to the supplement was 0.6 kg over four weeks (Kaats et al., oral presentation, 3rd International Conference on Anti-Aging Medicine and Biomedical Technology, Las Vegas, 1995). Used alone, either of these techniques appears to have some utility, but they should be considered as adjuvants to traditional weight management techniques. In contrast, the results reported herein with the combined use of these measures are clearly far greater than the sum of their individual efficacies and constitute a new and definitive approach to obesity control.

It is also notable that, in every subject, lean body mass increased during the study. Thus, the response was quite different from that seen during very low calorie dieting. The subjective increase in energy (which helped some subjects comply with the recommended exercise) and in body warmth is also hardly typical of response during caloric deprivation. Perhaps the most telling indication of the success of the regimen were the dozens of friends and relatives of the volunteers who demanded to be included in the study.

If one assumes that a pound of fat corresponds to about 3,500 kcal, whereas a pound of lean averages 700 kcal, the average daily caloric deficit was approximately 2,370 kcal (2,100 kcal if the heaviest subject is excluded from the analysis). Given the fact that the subjects were not subjected to severe caloric restriction (indeed, a few complained that they were being asked to eat too much), and were asked to do only walking exercise of modest duration, these responses are likely to be unprecedented and are strongly suggestive of a dramatic increase in thermogenesis. The average monthly weight loss, approximately 6.5 kg (14.3 lb) is exceptional in the context of a regimen that does not include severe caloric restriction, draconian exercise or drugs.

The above description of the invention is set forth solely to assist in understanding the invention. It is to be understood that variations of the invention, including all equivalents now known or later developed, are to be considered as falling within the scope of the invention, which is limited only by the following claims.

What is claimed is:

1. A method for promoting weight and fat loss in an individual in need thereof, comprising coadministering to said individual daily effective weight and fat loss-promoting amounts of hydroxycitrate, carnitine, chromic tripicolinate and an agent which promotes intramitochondrial generation of oxaloacetate or induces endogenous production of pyruvate.

2. The method of claim 1, wherein said effective amount of hydroxycitrate is between about 1 and 10 grams.

3. The method of claim 2, wherein said effective amount of hydroxycitrate is between about 1 and 5 grams.

4. The method of claim 1, wherein said effective amount of carnitine is between about 100 and 1,000 milligrams.

5. The method of claim 4, wherein said effective amount of carnitine is between about 100 and 500 milligrams.

6. The method of claim 1, wherein said agent which promotes intramitochondrial generation of oxaloacetate is selected from the group consisting of pyruvate, lactic acid, aspartic acid, serine and glycine.

7. The method of claim 1, wherein said agent which promotes endogenous production of pyruvate is metformin or biotin.

8. The method of claim 6, wherein said effective amount of said agent is between about 1 and 100 grams.

9. The method of claim 8, wherein said effective amount of said agent is between about 1 and 25 grams.

10. The method of claim 7, wherein said effective amount of biotin is between about 5 and 50 milligrams.

11. The method of claim 7, wherein said effective amount of metformin is between about 1 and 3 milligrams.

12. The method of claim 1, wherein said effective amount of chromic tripicolinate is about 400–1,000 micrograms.

13. The method of claim 12, wherein said effective amount is about 600 micrograms.

14. A pharmaceutical composition comprising hydroxycitrate, carnitine, chromic tripicolinate and an agent which promotes the intramitochondrial generation of oxaloacetate or induces endogenous production of pyruvate, wherein the ratio of hydroxycitrate to carnitine to agent is between about 2:1:2 and 10:1:100 (w/w).

15. The pharmaceutical composition of claim 14, wherein said agent which promotes intramitochondrial generation of oxaloacetate is selected from the group consisting of pyruvate, lactic acid, aspartic acid, serine and glycine.

16. The pharmaceutical composition of claim 14, wherein said agent which promotes endogenous production of pyruvate is metformin or biotin.

* * * * *